United States Patent
Fraser et al.

(10) Patent No.: US 12,018,227 B2
(45) Date of Patent: Jun. 25, 2024

(54) ENCAPSULATED FRAGRANCE COMPOSITION

(71) Applicant: TAKASAGO INTERNATIONAL CORPORATION, Tokyo (JP)

(72) Inventors: Stuart Fraser, Little Neston (GB); Johan Poncelet, Paris (FR); Tiphaine Ribaut, Paris (FR); Jonathan Warr, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 17/236,904

(22) Filed: Apr. 21, 2021

(65) Prior Publication Data
US 2021/0324299 A1    Oct. 21, 2021

(30) Foreign Application Priority Data
Apr. 21, 2020    (EP) .................................... 20305383

(51) Int. Cl.
*C11B 9/00*    (2006.01)

(52) U.S. Cl.
CPC .......... *C11B 9/0034* (2013.01); *C11B 9/0007* (2013.01)

(58) Field of Classification Search
CPC ............................ C11B 9/0034; C11B 9/0007
USPC ............................................................. 512/4
See application file for complete search history.

(56) References Cited

U.S. PATENT DOCUMENTS

| 6,455,080 B1 | 9/2002 | Wolf et al. |
| 2010/0280110 A1 | 11/2010 | Hojo et al. |
| 2011/0081393 A1 | 4/2011 | Komatsuki et al. |
| 2014/0170101 A1* | 6/2014 | Cetti ................. A61K 8/28 424/65 |
| 2018/0030373 A1* | 2/2018 | Lombardo ............... A61L 9/01 |

FOREIGN PATENT DOCUMENTS

| EP | 1 121 927 A2 | 8/2001 |
| EP | 1 496 095 A1 | 1/2005 |
| EP | 3 219 332 A2 | 9/2017 |
| EP | 3 219 333 A2 | 9/2017 |
| WO | WO 2006/127282 A2 | 11/2006 |
| WO | WO 2009/123355 A2 | 10/2009 |
| WO | WO 2013/087364 A1 | 6/2013 |
| WO | WO 2016/138186 A1 | 9/2016 |

OTHER PUBLICATIONS

European Search Report dated Sep. 30, 2020 in Application No. EP 20305383.

* cited by examiner

*Primary Examiner* — Ling Siu Cho
*Assistant Examiner* — Ronald Grinsted
(74) *Attorney, Agent, or Firm* — Baker Botts L.L.P

(57) ABSTRACT

The present disclosure is directed to an encapsulated fragrance composition including an accord including at least one of menthol and isopulegol. Consumer products containing said encapsulated fragrance composition are also disclosed herein.

18 Claims, No Drawings

ENCAPSULATED FRAGRANCE COMPOSITION

CROSS REFERENCE TO RELATED APPLICATIONS

This application claims priority to European Application No. 20 305 383.0 filed on Apr. 21, 2020, the contents of which are hereby incorporated by reference herein in its entirety.

FIELD

The present disclosure relates to capsules including a fragrance composition and to the use of such capsules in consumer products.

BACKGROUND

There is continuing interest in the preparation of fragrance compositions and in the use of such compositions in consumer products. Shortcomings of existing fragrance compositions can be limited intensity, noticeability, and perceptibility. For example, certain fragrance compositions can have appealing odors but can have limited intensity and high perception thresholds, which can limit the impact of the fragrance composition at distance from its source. Other fragrance compositions can have greater intensity and lower perception thresholds but can have less appealing odors. Moreover, fragrance compositions can become less noticeable due to a user's decrease in sensitivity over prolonged exposure. Adaptation and habituation can necessitate replacement of the fragrance source.

EP-A-3 219 332 discloses household products including a fragrance composition in which said composition includes from 0.2 to less than 10% by weight of isopulegol. The fragrance composition can further include one or more cooling agents. EP-A-3 219 333 discloses household products including a fragrance composition in which said composition includes from 0.01 to less than 10% by weight of at least one chemaesthetic agent selected from vanillyl ethyl ether, vanillyl n-propyl ether, vanillyl isopropyl ether, vanillyl butyl ether, elemol, elemicin, lime oxide, ocimene quintoxide, 2-isopropenyl-5-methyl-5-vinyltetrahydrofuran and isopulegol. U.S. 2018/0030373 A1 discloses a fragrance composition which includes one or more trigeminal-stimulating compounds including one or more of a cooling compound, a warming compound and/or a tingling compound. The examples in this patent application show the trigeminal-stimulating effect of a combination of (−)-menthol, vanillyl ethyl ether (HOTACT® VEE) and vanillyl butyl ether (HOTACT® VBE).

US 2018/0265805A1 discloses a method for releasing fragrances from capsules under controlled condition, the method including incorporating an orthoformic acid ester into the core of the capsules.

WO 2013/087364 discloses a method for increasing the shear release effect associated with a fabric conditioning formulation containing conventional encapsulated volatile benefit agents, which includes including a phase change material (i.e., a material that can absorb, store and release heat whilst the material changes its physical form, typically hydrocarbon materials having 12 to 50 carbon atoms per molecule) in the core of the capsules.

There is still a need for fragrance compositions with appealing odors and improved intensity, noticeability, and perception thresholds. It has been found that inclusion of a combination of specific trigeminal-stimulating compounds into a fragrance composition can improve the hedonic experience, intensity, and noticeability of the odor.

On applying a selection of volatile trigeminal stimulating compounds into fragrances used in rinse off consumer products, such as laundry detergent products and fabric softeners, no benefit is noticeable on the dried fabric. Experiments have shown that the trigeminal stimulating compounds are either not sufficiently well deposited, or they evaporate rapidly from the surface during drying so that too little remains on the substrate to be noticed.

It has now been found that specific volatile trigeminal stimulating compounds, when incorporated into a fragrance composition which is encapsulated, can provide a means of delivering the benefits of perceptibly more intense fragrances, with appealing odors and improved adaptability and habituation thresholds, and a greater perception of freshness.

SUMMARY

In certain embodiments, the present disclosure relates to an encapsulated fragrance composition, which includes from about 1.00 wt % to about 10.00 wt %, based on the weight of the fragrance composition, of an accord, wherein the accord includes (i) from about 90.00 wt % to about 100 wt %, based on the weight of the accord, of at least one compound selected from menthol (2-isopropyl-5-methylcyclohexan-1-ol, CAS 89-78-1), menthyl acetate (2-isopropyl-5-methylcyclohexyl) acetate, CAS 16409-45-3), isopulegol (2-isopropenyl-5-methyl cyclohexan-1-ol, CAS 7786-67-6), pulegone (CAS 89-82-7), pulegol (2-isopropylidene-5-methyl cyclohexanone, CAS 529-02-2), peppermint cyclohexanone (2-sec butylcyclohexanone, CAS 14765-30-1), dihydromyrcene (3,7-dimethylocta-1,6-diene, CAS 2436-90-0), and combinations thereof, wherein the accord includes at least two compounds, and wherein at least one of menthol and isopulegol is present in the accord.

In certain embodiments, the accord further includes (ii) about 0.01 wt % to about 10.00 wt %, based on the weight of the accord, of at least one compound selected from citroxide (2,2-dimethyl-5-(1-methylpropen-1-yl)tetrahydrofuran, CAS 7416-35-5), elemicin (1,2,3 trim ethoxy-5-prop-2-enyl benzene, CAS 487-11-6), elemol (2-(4-ethenyl-4-methyl-3-prop-1-en-2-yl cyclohexyl) propanol, CAS 639-99-6), geranic oxide (2,2,6-trimethyl-6-vinyltetrahydropyran, CAS 7392-19-0), vanillyl ethyl ether (4-(ethoxymethyl)-2-methoxyphenol, CAS 13184-86-6), vanillyl butyl ether (4-(butoxymethyl)-2-methoxyphenol, CAS 82654-98-6), caryophyllene beta (11R-(1R,4E,9S)-4,11,11-trimethyl-8-methylenebicyclo7.2.0)undece-4-ene, CAS 87-44-5), zingiberene alpha ((5R)-2-methyl-5-[(2 S)-6-methylhept-5 ene-2yl]cyclohexa-1,3-di ene, CAS 495-60-3), and combinations thereof, wherein the sum of (i)+(ii) makes up 100 wt % of the accord.

In certain embodiments, the accord includes from about 90.00 wt % to about 99.99 wt % of at least one compound (i) and from about 0.01 wt % to about 10.00 wt % of at least one compound (ii).

In certain embodiments, the accord includes menthol and menthol represents at least 40.00 wt % of the combined weight of all compounds (i) in the accord.

In certain embodiments, the accord includes isopulegol and isopulegol represents at least 40.00 wt % of the combined weight of all compounds (i) in the accord.

In certain embodiments, the accord includes menthol and isopulegol and optionally at least one other compound (i), wherein the weight ratio between menthol and isopulegol is in the range from about 30:70 to about 70:30.

In certain embodiments, the sole compounds (i) of the accord are menthol and isopulegol.

In certain embodiments, the at least one compound (ii) is selected from the group consisting of elemicin, elemol and citroxide.

In certain embodiments, the accord consists of menthol, isopulegol and citroxide.

In certain embodiments, the fragrance composition of the present disclosure is encapsulated in starch capsules, silica capsules or core shell capsules.

In certain embodiments, the fragrance composition is encapsulated in core shell capsules, the shell of which includes a material selected from polyolefins, polyamides, polystyrenes, polyisoprenes, polycarbonates, polyesters, polyacrylates, aminoplasts, polysaccharides, gelatine, shellac, epoxy resins, vinyl polymers, water insoluble inorganics, silicone, and mixtures thereof.

In certain embodiments, the shell includes melamine formaldehyde and/or cross-linked melamine formaldehyde. In certain embodiments, the shell includes a polyacrylate.

In certain embodiments, the shell is coated with a deposition aid.

In certain embodiments, the present disclosure is directed to a consumer product including the encapsulated fragrance composition of the present disclosure. In certain embodiments, the consumer product is selected from the group consisting of a laundry product and a personal cleansing product. Non-limiting examples of such laundry products include a laundry detergent, a fabric softener, and a fabric conditioner. Non-limiting products of such personal cleansing products, include as a bar soap, liquid soap, a shower gel, a shampoo or a hair conditioner.

DETAILED DESCRIPTION

As used herein, the use of the word "a" or "an" when used in conjunction with the term "comprising" in the claims and/or the specification can mean "one," but it is also consistent with the meaning of "one or more," "at least one," a plurality, and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the terms "include", "includes" and "including" are meant to be synonymous with the phrase "including but not limited to".

As used herein, the term "accord" is intended to mean a mixture of at least two compounds which can induce a variety of different sensations such as tingling, warming, and/or cooling. One or more "accords" can be utilized as part of fragrance composition.

As used herein, the term "habituation" refers to a user or tester's long-term loss of awareness of a background odour. Habituation can be considered a form of learning that can arise from prolonged exposure to an odour. Habituation can be related to adaptation. Like adaptation, habituation can result in lower sensitivity to an odour, as a lower level of attention is directed to the odour.

As used herein, the term "consumer product" or "end product" refers to a composition that is in a form ready for use by the consumer for the marketed indication. A solvent suitable for use in a consumer product is a solvent that, when combined with other components of the end product, will not render the consumer product unfit for its intended consumer use.

In one aspect, the present disclosure is directed to an encapsulated fragrance composition, said fragrance composition including from about 1.00 wt % to about 10.00 wt %, based on the weight of the fragrance composition, of an accord including:

(i) from about 90.00 wt % to about 100 wt %, based on the weight of the accord, of at least one compound selected from the group consisting of menthol, menthyl acetate, isopulegol, pulegone, pulegol, peppermint cyclohexanone, and dihydromyrcene; and (ii) optionally up to about 10.00 wt %, based on the weight of the accord, of at least one compound selected from citroxide, elemicin, elemol, geranic oxide, vanillyl ethyl ether, vanillyl butyl ether, caryophyllene beta and zingiberene alpha;

wherein the accord includes at least two compounds, wherein at least one of menthol and isopulegol is present in the accord, and wherein the sum of (i)+(ii) makes up 100 wt % of the accord.

In certain embodiments, the fragrance composition includes from about 1.00 wt % to about 9.00 wt %, from about 2.00 wt % to about 8.00 wt %, from about 3.00 wt % to about 8.00 wt %, or from about 3.00 wt % to about 7.00 wt %, of the accord, based on the weight of the fragrance composition.

In certain embodiments, the accord includes about 90.00 wt % to about 99.99 wt %, for example 90.00 wt %, 91.00 wt %, 92.00 wt %, 93.00 wt %, 94.00 wt %, 95.00 wt %, 96.00 wt %, 97.00 wt %, 98.00 wt %, 99.00 wt %, 99.90 wt % or 99.99 wt %, of at least one compound (i). In this case the accord includes about 0.01 wt % to about 10.00 wt %, for example 0.01 wt %, 0.1 wt %, 1.00 wt %, 2.00 wt %, 3.00 wt %, 4.00 wt %, 5.00 wt %, 6.00 wt %, 7.00 wt %, 8.00 wt %, 9.00 wt % or 10.00 wt %, of at least one compound (ii).

In certain embodiments, the accord includes from about 90.00 wt % to about 100 wt %, from about 92.00 wt % to about 100 wt %, from about 95.00 wt % to about 100 wt % from about 98.00 wt % to about 100 wt % based on the weight of the accord, of a mixture of menthol, menthyl acetate, isopulegol, pulegone, pulegol, peppermint cyclohexanone, and dihydromyrcene.

In certain embodiments, the accord includes from about 0.01 wt % to about 10.00 wt %, from about 0.50 wt % to about 10.00 wt %, from about 1.00 wt %, to about 10.00 wt %, from about 1.50 wt %, to about 10.00 wt %, from about 2.00 wt %, to about 10.00 wt %, from about 2.50 wt %, to about 10.00 wt %, from about 5.00 wt %, to about 10.00 wt %, from about 7.50 wt %, to about 10.00 wt %, from about 9.00 wt %, to about 10.00 wt %, from about 0.01 wt % to about 9.00 wt %, from about 0.01 wt % to about 7.50 wt %, from about 0.01 wt % to about 5.00 wt %, from about 0.01 wt % to about 2.50 wt %, from about 0.01 wt % to about 1.50 wt %, from about 0.01 wt % to about 1.00 wt %, based on the weight of the accord, of at least one compound selected from citroxide, elemicin, elemol, geranic oxide, vanillyl ethyl ether, vanillyl butyl ether, caryophyllene beta and zingiberene alpha.

In certain embodiments, the amount of menthol, menthyl acetate, isopulegol, pulegone, pulegol, peppermint cyclohexanone, and dihydromyrcene makes up 100 wt % of the accord.

In certain embodiments, the accord includes menthol and menthol represents at least about 40.00 wt % of the combined weight of all compounds (i) in the accord.

In certain embodiments, the accord includes isopulegol and isopulegol represents at least about 40.00 wt % of the combined weight of all compounds (i) in the accord.

In certain embodiments, the accord includes peppermint cyclohexanone and peppermint cyclohexanone represents at least about 40.00 wt % of the combined weight of all compounds (i) in the accord.

In certain embodiments, the accord includes menthol and isopulegol, wherein the weight ratio between menthol and isopulegol is in the range from about 30:70 to about 70:30, or from about 40:60 to about 60:40. In a certain particular embodiment, the sole compounds (i) of the accord are menthol and isopulegol, in the weight ratio mentioned above.

In certain embodiments, the at least one compound (ii) is selected from elemicin, elemol and citroxide.

In certain embodiments, the accord consists of menthol, isopulegol and citroxide.

Menthol is available either as the racemate (CAS 89-78-1) or as the (−) isomer (CAS 2216-51-5), the latter being the main form occurring in nature.

Isopulegol is available either as a racemic mixture (CAS 7786-67-6), or as the (−)-isomer (CAS 89-79-2). In certain embodiments isopulegol is available as Coolact® P, a product from Takasago. The isopulegol of the disclosure can have an optical isomer and chemical purity of greater than 90%, greater than 95%, greater than 97.5%, or greater than 99%. Isopulegol purity is determined by gas chromatography using the method described in U.S. Pat. No. 5,773,410 by summing the area percent of impurity peaks and subtracting these from the total measured area which is taken to be 100%.

Peppermint cyclohexanone is commercially available as Freskomenthe®.

Dihydromyrcene is derived from pine distillates and widely used as an intermediate for other syntheses. It exists as two stereoisomers (+) and (−), and is also known as citronellene. Dihydromyrcene is one of the components of Dimene, a product which is available e.g., from the company Bordas. Other fragrance compounds can also provide a source for dihydromyrcene. The content of dihydromyrcene in Dimene typically ranges from about 20.00 wt % to about 45.00 wt %. All stereoisomeric forms of dihydromyrcene are within the scope of the present application.

Citroxide, also known as ocimene quintoxide, is one of the components of lime oxide (CAS 73018-51-6) which is commercially available e.g., from the company Ventos or the company Givaudan. The content of citroxide in lime oxide typically ranges from about 5.00 wt % to about 20.00 wt %. All stereoisomeric forms of citroxide are within the scope of the present application.

Geranic oxide, also known as limetol, is commercially available from e.g., the company Givaudan.

Elemol and elemicin are compounds found notably but not exclusively in elemi oil. Caryophyllene beta is a component of pepper oil. Zingiberene alpha is a component of ginger oil.

The fragrance composition typically includes, in addition to the accord described above, one or more fragrance compounds. In certain embodiments, the fragrance composition can include at least two, at least five, or at least eight distinct fragrance compounds. In certain embodiments, the fragrance composition can include highly complex mixtures of fragrance compounds, chosen to provide any desired odour. In the context of the present disclosure the term "fragrance" is intended to be synonymous with "perfume". Fragrance compounds typically used in the field of perfumery and suitable for the purposes of the present disclosure are described more fully in S. Arctander, Perfume Flavors and Chemicals 1969, Vols. I and II, Montclair, N. J. and in The Merck Index, 8$^{th}$ edition, Merck & Co., Inc. Rahway, N. J. The term "fragrance compound" encompasses naturally occurring as well as synthetic materials known for use in perfumes, as well as animal oils. A fragrance compound can also be any natural oil or extract used in a fragrance composition. Natural oils and extracts are described in The Essential Oils by E Guenther published in 1949 by Van Nostrand and can include extracts, pressings, collection of exudates, and distillates from any part of suitable plants: roots, rhizomes, bulbs, corms, stem, bark, heartwood, leaves, flowers, seeds and fruit. Examples of such extracts and distillates include citrus fruit oils such as orange, mandarin, grapefruit, lime or lemon oils, tree oils such as pine, or cedarwood, herb oils such as peppermint, thyme, lavender, basil, rosemary, clove or flower extracts such as rose, jasmine, muguet, or geranium oil.

In certain embodiments, each fragrance compound has a molecular weight greater than 100 g/mol, greater than 120 g/mol and lower than 325 g/mol, or lower than 300 g/mol. In certain embodiments, each fragrance compound has a boiling point in the range 80-400° C., such as in the range 100-350° C., when measured at 760 mm Hg.

Advantageously, the fragrance compounds are selected from the following list:

$C_8$-$C_{18}$ hydrocarbons, such as but not limited to delta-3-carene, alpha-pinene, beta-pinene, alpha-terpinene, gamma-terpinene, p-cymene, bisabolene, camphene, cedrene, farnesene, limonene, longifolene, myrcene, ocimene, valencene, (E,Z)-1,3,5-undecatriene;

$C_2$-$C_{18}$ aliphatic alcohols, such as but not limited to hexanol, octanol, 3-octanol, 2,6-dimethylheptanol, 2-methylheptanol, 2-methyloctanol, (E)-3-hexenol, (E) and (Z)-3-hexenol, 1-octen-3-ol, mixtures of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol;

$C_2$-$C_{18}$ aliphatic aldehydes and their acetals, such as but not limited to hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal diethyl acetal, 1,1-dimethoxy-2,2,5-trimethyl-4-hexene, citronellyl oxyacetaldehyde;

$C_3$-$C_{18}$ aliphatic ketones and oximes thereof, such as but not limited to 2-heptanone, 2-octanone, 3-octanone, 2-nonanone, 5-methyl-3-heptanone, 5-methyl-3-heptanone oxime, 2,4,4,7-tetramethyl-6-octen-3-one;

$C_2$-$C_{18}$ aliphatic sulphur-containing compounds, such as but not limited to 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol;

$C_2$-$C_{18}$ aliphatic nitrile-containing compounds, such as but not limited to 2-nonenenitrile, 2-tridecenenenitrile, 2,12-tridecenene-nitrile, 3,7-dimethyl-2,6-octadienenitrile, 3,7-dimethyl-6-octenenitrile;

$C_2$-$C_{18}$ aliphatic carboxylic acids and esters thereof, such as but not limited to (E)- and (Z)-3-hexenyl formate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl 2-methylpentanoate, ethyl hexanoate, allyl hexanoate, ethyl heptanoate, allyl heptanoate, ethyl octanoate, ethyl (E,Z)-2,4-decadienoate, methyl 2-octynoate, methyl 2-nonynoate, allyl-2-isoamyloxyacetate, methyl-3,7-dimethyl-2,6-octadienoate;

$C_4$-$C_{18}$ acyclic terpene alcohols, such as but not limited to citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol;

$C_4$-$C_{18}$ acyclic terpene aldehydes and ketones, such as but not limited to geranial, neral, citronellal, 7-hydroxy-3,7-dimethyloctanal, 7-m ethoxy-3,7-dimethyloctanal, 2,6,10-trimethyl-9-undecenal, geranylacetone, and the dimethyl and diethyl acetals of geranial, neral, 7-hydroxy-3,7-dimethyloctanal;

$C_4$-$C_{18}$ cyclic terpene alcohols, such as but not limited to alpha-terpineol, terpineol-4, menthan-8-ol, menthan-1-ol, menthan-7-ol, borneol, isoborneol, linalool oxide, nopol, cedrol, ambrinol, vetiverol, guaiol;

$C_4$-$C_{18}$ cyclic terpene aldehydes and ketones, such as but not limited to fenchone, alpha-ionone, beta-ionone, alpha-n-methylionone, beta-n-methylionone, alpha-isomethylionone, beta-isomethylionone, alpha-irone, alpha-damascone, beta-damascone, beta-damascenone, delta-damascone, gamma-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone, alpha-sinensal, beta-sinensal, methyl cedryl ketone;

$C_4$-$C_{18}$ cyclic alcohols, such as but not limited to 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

$C_4$-$C_{18}$ cycloaliphatic alcohols, such as but not limited to alpha-3,3-trimethylcyclohexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

$C_4$-$C_{18}$ cyclic and cycloaliphatic ethers, such as but not limited to cedryl methyl ether, cyclododecyl methyl ether, (ethoxymethoxy)cyclododecane, alpha-cedrene epoxide, 3a, 6,6,9a-tetramethyl-dodecahydronaphtho[2,1-b] furan, 3a-ethyl-6,6,9a-trimethyl dodecahydronaphtho[2,1-b] furan, 1,5,9-trimethyl-13-oxabicyclo[10.1.0]trideca-4,8-di ene, rose oxide, 2-(2,4-dimethyl-3-cyclohexen-1-yl)-5-methyl-5-(1-methylpropyl)-1,3-dioxane;

$C_4$-$C_{18}$ cyclic ketones, such as but not limited to 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 9-cycloheptadecen-1-one, cyclopentadecanone, cyclohexadecanone;

$C_4$-$C_{18}$ cycloaliphatic aldehydes, such as but not limited to 2,4-dimethyl-3-cyclohexenecarbaldehyde, 2-methyl-4-(2,2,6-trimethyl-cyclohexen-1-yl)-2-butenal, 4-(4-hydroxy-4-methylpentyl)-3-cyclohexenecarbaldehyde, 4-(4-methyl-3-penten-1-yl)-3-cyclohexenecarbaldehyde;

$C_4$-$C_{18}$ cycloaliphatic ketones, such as but not limited to 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl-2,6,10-trimethyl-2,5,9-cyclododecatrienyl ketone, tert-butyl (2,4-dimethyl-3-cyclohexen-1-yl)ketone;

esters of cyclic alcohols in $C_4$-$C_{18}$, such as but not limited to 2-tert-butylcyclohexyl acetate, 4-tert-butyl-cyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl isobutyrate, 4,7-methanooctahydro-5 or 6-indenyl acetate;

esters of cycloaliphatic carboxylic acids in $C_4$-$C_{18}$, such as but not limited to allyl 3-cyclohexylpropionate, allyl cyclohexyloxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

$C_4$-$C_{18}$ aromatic hydrocarbons, such as but not limited to styrene and diphenylmethane;

$C_4$-$C_{18}$ araliphatic alcohols, such as but not limited to benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

esters of araliphatic alcohols in $C_4$-$C_{18}$ and aliphatic carboxylic acids in $C_4$-$C_{18}$, such as but not limited to benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, alpha-trichloromethylbenzyl acetate, alpha, alpha-dimethylphenylethyl acetate, alpha, alpha-dimethylphenylethyl butyrate, cinnamyl acetate, 2-phenoxyethyl isobutyrate, 4-methoxybenzyl acetate;

$C_2$-$C_{18}$ araliphatic ethers, such as but not limited to 2-phenylethyl methyl ether, 2-phenylethyl isoamyl ether, 2-phenylethyl 1-ethoxyethyl ether, phenylacetaldehyde dimethyl acetal, phenylacetaldehyde diethyl acetal, hydratropaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

$C_4$-$C_{18}$ aromatic and araliphatic aldehydes, such as but not limited to benzaldehyde, phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert.-butylphenyl) propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylenedioxybenzaldehyde, 3,4-dimethoxybenzaldehyde, 2-methyl-3-(4-methoxyphenyl)propanal, 2-methyl-3-(4-methylenedioxyphenyl)propanal;

$C_4$-$C_{18}$ aromatic and araliphatic ketones, such as but not limited to acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl ethyl)-1H-5-indenyl]ethanone, 5',6',7',8'-tetrahydro-3',5',5',6',8',8'-hexamethyl-2-acetonaphthone;

$C_4$-$C_{18}$ aromatic and araliphatic carboxylic acids and esters thereof, such as but not limited to phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

nitrogen-containing aromatic compounds in $C_4$-$C_{18}$, such as but not limited to 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenenitrile, 5-phenyl-3-methylpentanenitrile, methyl anthranilate, methyl N-methylanthranilate, Schiff bases of methyl anthranilate with 7-hydroxy-3,7-dimethyloctanal, 2-methyl-3-(4-tert-butylphenyl)propanal, 2,4-dimethyl-3-cyclohexene-carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

phenols, phenyl ethers and phenyl esters, such as but not limited to estragole, anethole, eugenol, eugenyl methyl ether, isoeugenol, isoeugenyl methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

heterocyclic compounds in $C_4$-$C_{12}$, such as but not limited to 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

lactones in $C_4$-$C_{18}$, such as but not limited to 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene 1,12-dodecanedioate, ethylene 1,13-tridecanedioate, coumarin, 2,3-dihydrocoumarin, octahydrocoumarin.

In certain embodiments, the fragrance compounds present in the fragrance composition do not contain ionizing functional groups, such as sulfonates, sulphates, phosphates or quaternary ammonium ions.

In certain embodiments, the fragrance composition of the disclosure can include one or more support materials, such as solvents or UV stabilizers. Examples of suitable solvents include hydrocarbons such as those sold under the trade name Isopar®; ethers such as those sold under the Dowanol® trade name; benzyl benzoate; isopropyl myristate; dialkyl adipates; dialkyl succinates; dialkyl glutarates such as the dimethyl esters sold under the trade name Flexisolv®; citrate esters, such as triethyl citrate and acetyl tributyl citrate; soybean methyl ester such as ME-51885 (sold by Peter Cremer NA); diethyl phthalate; diethylene glycol monoethyl ether; 3-methoxy-3-methyl-1-butanol; dipropylene glycol; and isopropylidene glycerol sold under the Augeo® Clean Multi brand name. Examples of UV stabilisers include butyl methoxy dibenzoyl methane; bis ethylhexyloxyphenolmethoxyphenyl triazine; those sold under the Uvinol® trade name such as Uvinul D50 [bis(2,4-dihydroxyphenyl)-methanone], Uvinul MC80 (ethylhexyl methoxycinnamate) and Uvinul M40 (benzophenone-3); those sold under the Parsol® trade name, such as Parsol® MCX (same product as Uvinul MC80) and Parsol® 1789 (butyl methoxydibenzoylmethane); and those sold under the Tinogard® trade name, such as Tinogard® TT (pentaerythrityl tetra di-t-butyl hydroxyhydrocinnamate).

In certain embodiments, the fragrance composition is encapsulated in a delivery system, which system can then be incorporated into e.g., laundry products with the view of eventually delivering a noticeable odour to the consumer. Non-limiting examples of delivery systems include starch capsules, silica capsules and core shell capsules.

General descriptions and methods of preparation of microcapsules can be found in "MICROENCAPSULATION: Methods and Industrial Applications Edited by Benita and Simon (Marcel Dekker, Inc. 1996)". Microcapsules are also described in Kirk Othmer's Encyclopaedia of Chemical Technology 5th edition. Capsules can be formed by mechanical or chemical means. Mechanically formed capsules can be formed by means, such as spray chilling e.g., in U.S. 2004/0106536, by compression of solids or by spray drying emulsions e.g., in U.S. Pat. No. 6,200,949. Chemically formed capsules are produced by chemical reactions forming ionic or covalent bonds using techniques such as co-acervation, interfacial polymerisation, condensation reactions and free radical polymerisation. One particularly efficient and commercially important type of microcapsule, is referred to as a wall or shell or core shell microcapsule, and includes a generally spherical shell of water- and oil-insoluble materials, typically a network polymer material, within which fragrance or other hydrophobic material is contained. It can be understood that these various methods of encapsulation can be combined as can the different chemical reactions used to prepare capsule walls. Encapsulation can combine physical and chemical means of capsule preparation or combine more than one type of chemical reaction to prepare multi walled capsules or hybrid capsule walls. Capsules can also be obtained by co-acervation methods. More specific descriptions of such methods can be found in U.S. Pat. Nos. 2,800,457; 2,800,458, 3,041,288 and WO 99/17871. Descriptions of interfacial polymerisation methods can be found in U.S. Pat. Nos. 4,681,806; 3,415,758; 8,426,353; U.S. 2008/020629 and EP-A-2 038 053. Examples of capsules formed by condensation reactions can be found in U.S. Pat. Nos. 3,516,941; 3,516,846; 6,261,483; U.S. 2004/087477; GB-A-2,073,132 and EP-A-1 393 706. Capsules formed by free radical polymerisation are described in U.S. Pat. Nos. 6,849,591; 6,951,836 and U.S. 2010/002860.

In certain embodiments, the fragrance composition is encapsulated in core shell capsules, i.e., capsules having a core (including, such as consisting essentially of, the fragrance composition) surrounded by a shell which can be made from various materials.

In certain embodiments, the shell of the microcapsules includes a material selected from polyolefins such as polyethylenes, polyamides, polystyrenes, polyisoprenes, polycarbonates, polyesters, polyacrylates, polyurethanes, aminoplasts, polysaccharides such as alginate and/or chitosan, gelatine, shellac, epoxy resins, vinyl polymers, water insoluble inorganics, silicone, and mixtures thereof.

In certain embodiments, the shell of the microcapsules includes urea-formaldehyde, melamine formaldehyde or cross-linked melamine formaldehyde.

In certain embodiments, the shell of the microcapsules includes a polyacrylate. Non-limiting examples of polyacrylate shells are disclosed e.g., in EP-A-2 620 211, EP-A-2 832 440, EP-A-2 832 441 and EP-A-2 832 442, the content of which is incorporated by reference.

In certain embodiments, the shell of the microcapsules includes the reaction product of a Michael donor and a Michael acceptor, wherein the reaction is optionally carried out in the presence of solid colloidal particles and/or a catalyst. For example, the shell can include the reaction product of (i) an α,β-unsaturated carbonyl compound and a multifunctional amine, optionally in the presence of solid colloidal particles; or (ii) an α,β-unsaturated carbonyl compound and a multifunctional thiol compound, optionally in the presence of a catalyst.

In certain embodiments, the shell of the microcapsules includes the reaction product of a multifunctional isocyanate and a multifunctional thiol compound, optionally in the presence of solid colloidal particles and/or a catalyst.

In certain embodiments, the shell of the microcapsules is as defined in WO 2019/121736, WO 2019/121738, WO 2020/020829 or else KR 20190023697.

In certain other embodiments, the shell of the microcapsules is as defined in European patent applications number 20305187.5, 20305188.3 or else 20305189.1, the content of which is incorporated by reference.

In certain embodiments, a deposition aid is coated on the shell of the microcapsules to increase deposition or adhesion of the microcapsules to various surfaces such as various substrates including but not limited to paper, fabric skin, hair, towels, or other surfaces. Suitable deposition aids include poly(acrylamide-co-diallyldimethylammonium) chloride, poly(diallyldimethylammonium) chloride, polyethylenimine, cationic polyamine, poly[(3-methyl-1-vinylimidazolium chloride)-co-(1-vinylpyrrolidone)], copolymer of acrylic acid and diallyldimethylammonium chloride, cationic guar, guar gum, an organopolysiloxane such as described in U.S. patent application 2015/0030557. Deposition aids can also be selected from poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methylacrylate, polyvinylpyrrolidone-vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinylpyrrolidone/methacrylamidopropyltrimethylammonium chloride), polyvinylpyrrolidone/vinyl acetate, polyvinyl pyrrolidone/ dimethylaminoethyl methacrylate, polyvinyl amines, polyvinyl formamides, polyallyl amines and copolymers of polyvinyl amines, polyvinyl formamides, and polyallyl amines, and mixtures thereof.

In certain embodiments, the encapsulated fragrance compositions disclosed herein can advantageously be incorporated into a variety of products notably laundry products and personal cleansing products. The microcapsules are advantageously prepared as a dispersion, which dispersion is then incorporated into the desired product.

The amount of microcapsules dosed into said products can vary depending on several aspects such as the desired microcapsule concentration, the proportion of fragrance within the microcapsules and the amount of fragrance necessary to create the olfactory effect desired. After removing all liquid components from a given product (i.e., measured as dry weight) the microcapsules can be present in an amount from about 0.01 to about 10% by weight, from about 0.05% to about 2.5% by weight, or from about 0.1 to about 1.25% by weight of the weight of the product. The dispersion of microcapsules can be incorporated at a suitable stage in the product manufacturing process but usually after any high shear mixing stage. In certain embodiments, when the product is liquid at room temperature, the product into which the microcapsules are to be added can have a viscosity greater than about 20 MPa, for example greater than about 100 MPa, or greater than about 1,000 MPa, or even greater than about 10,000 MPa, when measured at a low (e.g., 10 rpm) spindle speed and at 25° C. If necessary, viscosity can be adjusted through the addition of conventional viscosity modifying agents. Suitable agents as well as equipment and conditions to measure the viscosity of a product are discussed in Rheology Modifiers Handbook Practical Uses and Applications by M R Rosen and D Braun published by William Andrew Publishing in 2000 with ISBN 978-0-8155-1441-1.

In certain embodiments, the present disclosure relates to a laundry product including an encapsulated fragrance composition as defined above. In one aspect the laundry product is a laundry detergent (either powdered, pelleted or liquid), a fabric softener or a fabric conditioner.

Fabric softeners and conditioners specifically include both conventional diluted (e.g., 2% to 8% by weight) liquid active concentration softeners and concentrated (e.g., 10% to 40% by weight) liquid active concentration softeners as well as fabric conditioners which can contain ingredients to protect colours or garment shape and appearance (reference can be made for example to U.S. Pat. Nos. 6,335,315; 5,674,832; 5,759,990; 5,877,145; 5,574,179). Laundry detergents, particularly liquid laundry detergents, specifically include light duty liquid detergents and heavy-duty liquid detergents which can be structured multi-phase liquids or isotropic liquids and which can be aqueous or non-aqueous liquids. These liquids can be in bottles or unit dose sachets and they can optionally contain bleaching agents or enzymes (reference can be made for example to U.S. Pat. Nos. 5,929,022; 5,916,862; 5,731,278; 5,470,507; 5,466,802; 5,460,752; 5,458,810).

The formulations and ingredients of laundry products in which capsules of the present disclosure can be used are well known to those skilled in the art, reference can be made to the following works:

Formulating Detergents and Personal Care Products A guide to Product Development by L Ho Tan Tai, ISBN 1-893997-10-3 published by the AOCS Press Volume 67 of the Surfactant Science Series Liquid Detergents ISBN 0-8247-9391-9 (Marcel Dekker Inc), Volume 71 of the Surfactant Science Series Liquid Detergents ISBN 0-8247-9988-7 (Marcel Dekker Inc).

In another embodiment, the present disclosure relates to a personal cleansing product, notably a bar soap, liquid soap, a gel shower, a shampoo or a hair conditioner, including an encapsulated fragrance composition as defined above. Descriptions of personal cleansing products can be found inter alia in Harry's Cosmeticology published by CHS Press 8$^{th}$ Edn. 2000 ISBN 0820603724, as well as in Woollatt, 'The Manufacture of Soaps, Other Detergents and Glycerine', John Wiley & Sons, 1985.

Shampoos or hair conditioners can be formulated for dry or greasy hair or contain additives such as antidandruff agents.

The present disclosure will be better understood in the light of the following examples given by way of illustration only. In these examples the percentages expressed are percentages by weight unless otherwise mentioned.

EXAMPLES

The present application is further described by means of the examples, presented below, wherein the abbreviations have the usual meaning in the art.

The use of such examples is illustrative only and does not limit the scope and meaning of the disclosed subject matter or of any exemplified term. Likewise, the disclosed subject matter is not limited to any particular preferred embodiments described herein. Indeed, many modifications and variations of the disclosed subject matter are apparent to those skilled in the art upon reading this specification. The disclosed subject matter is therefore to be limited only by the terms of the appended claims along with the full scope of equivalents to which the claims are entitled.

Capsule Particle Size Measurement

Median volume diameter and span were measured with a laser diffraction/scattering particle size distribution analyzer (trade name: LA-950V2, manufactured by Horiba, Ltd.). The dispersant was 18 MΩ water. Several droplets of the emulsion or the capsule dispersion were poured into the flow cell unit until an acceptable level of laser light obscuration was achieved and triplicate measurements were then immediately performed. For the calculation of the particle size measurement, the refractive indexes were set at 1.33 (for the water dispersant) and 1.47 (for the fragrances and the capsules). The capsule diameter was measured as a particle size of 50% frequency (median size) on a volumetric basis D(v; 0.5). The span was calculated according to the following formula:

$$\text{Span} = \frac{D(v; 0.9) - D(v; 0.1)}{D(v; 0.5)}$$

in which D(v; 0.9) is the particle size for 90% of the microcapsules by volume, D(v; 0.1) is the particle size for 10% of the microcapsules by volume and D(v; 0.5) is the median volume microcapsule size as previously defined.

Solid Content Measurement Method

Approximately 2.5 g of slurry are weighted in an aluminum weighing dish and dried during four hours at 105° C. in order to remove water. The weight of the dry sample is then determined at room temperature and compared to the weight of the dispersion.

In the following fragrance compositions, lime oxide containing about 9.7 wt % citroxide was obtained from the company Ventos.

Example 1: Fragrance Composition A (Wt %)

Example 1 provides an exemplary "base" fragrance composition according to certain embodiments of the present disclosure. This "base" fragrance composition has a 10% hole, marked as "Additional Compound(s) in Table 1.

TABLE 1

Fragrance Composition A

| Ingredient Name | CAS No. | Wt % |
|---|---|---|
| Verdox | 88-41-5 | 33.50 |
| Isobornyl acetate | 125-12-2 | 20.00 |
| Dimethyl benzyl carbinyl acetate | 151-05-3 | 14.00 |
| 2,4-ivy carbaldehyde | 68039-49-6, 144046-32-2 | 6.50 |
| 2-methyl undecanal | 110-41-8 | 4.50 |
| Ethyl 2-methylbutyrate | 7452-79-1 | 4.50 |
| Ethyl-2-methylpentanoate | 39255-32-8 | 3.00 |
| 2-(2-(4-methyl-3-cyclohexenyl-1-yl)propyl)cyclopentanone | 95962-14-4 | 2.50 |
| Delta damascone | 57378-68-4 | 1.50 |
| Additional Compound(s) | | 10.00 |
| Total | | 100.00 |

Example 2: Fragrance Composition B

Example 2 provides another exemplary "base" fragrance composition according to certain embodiments of the present disclosure. This "base" fragrance composition has a 10% hole, marked as "Additional Compound(s)" in Table 2.

TABLE 2

Fragrance Composition B

| Ingredient Name | CAS No. | Wt % |
|---|---|---|
| Isobornyl acetate | 125-12-2 | 31.40 |
| Verdox | 88-41-5 | 20.40 |
| Eucalyptol | 470-82-6 | 8.00 |
| Undecanal | 112-44-7 | 6.50 |
| Styrallyl acetate | 93-92-5 | 6.50 |
| 2-methyl undecanal | 110-41-8 | 6.00 |
| Undecalactone gamma | 104-67-6 | 3.00 |
| 2-ethyl pentyl-1,3-dioxolane | 4359-47-1 | 3.00 |
| Camphor gum powder synthetic | 464-49-3 | 2.00 |
| Ethyl 2-methylbutyrate | 7452-79-1 | 1.50 |
| 2-Acetonaphthone | 93-08-3 | 1.00 |
| Cycloocten-1-yl methyl carbonate | 87731-18-8 | 0.70 |
| Additional Compound(s) | | 10.00 |
| Total | | 100.00 |

Example 3: Control Fragrance Composition C1

Example 3 provides an exemplary control fragrance composition according to certain embodiments of the present disclosure. This particular fragrance composition was obtained by adding 10 wt % isopropyl myristate (IPM) as an "additional compound" to the Fragrance Composition A of Example 1.

Example 4: Fragrance Composition n° 1

Example 4 provides an exemplary fragrance composition according to certain embodiments of the present disclosure. This particular fragrance composition was obtained adding (i) 2 wt % of an accord including isopulegol, L-menthol and lime oxide (weight ratio: 1/1/0.1) and (ii) 8 wt % isopropyl myristate (IPM) as "additional compounds" to the Fragrance Composition A of Example 1.

Example 5: Fragrance Composition n° 2

Example 5 provides an exemplary fragrance composition according to certain embodiments of the present disclosure. This particular fragrance composition was obtained by adding (i) 5 wt % of an accord including isopulegol, L-menthol and lime oxide (weight ratio: 1/1/0.1) and (ii) 5 wt % IPM as "additional compounds" to the Fragrance Composition A of Example 1.

Example 6: Fragrance Composition n° 3

Example 6 provides an exemplary fragrance composition according to certain embodiments of the present disclosure. This particular fragrance composition was obtained by adding 10 wt % of an accord including isopulegol, L-menthol and lime oxide (weight ratio: 1/1/0.1) as "additional compounds" to the Fragrance Composition A of Example 1.

Example 7: Control Fragrance Composition C2

Example 7 provides an exemplary control fragrance composition according to certain embodiments of the present disclosure. This particular fragrance composition was obtained by adding 10 wt % IPM as an "additional compound" to the Fragrance Composition B of Example 2.

Example 8: Fragrance Composition n° 4

Example 8 provides an exemplary fragrance composition according to certain embodiments of the present disclosure. This particular fragrance composition was obtained by adding (i) 2 wt % of an accord including isopulegol, L-menthol and lime oxide (weight ratio: 1/1/0.1) and (ii) 8 wt % IPM as "additional compounds" to the Fragrance Composition B of Example 2.

Example 9: Fragrance Composition n° 5

Example 9 provides an exemplary fragrance composition according to certain embodiments of the present disclosure. This particular fragrance composition was obtained by adding (i) 5 wt % of an accord including isopulegol, L-menthol and lime oxide (weight ratio: 1/1/0.1) and (ii) 5 wt % IPM as "additional compounds" to the Fragrance Composition B of Example 2.

Example 10: Fragrance Composition n° 6

Example 10 provides an exemplary fragrance composition according to certain embodiments of the present disclosure. This particular fragrance composition was obtained by adding 10 wt % of an accord including isopulegol, L-menthol and lime oxide (weight ratio: 1/1/0.1) as "additional compounds" to the Fragrance Composition B of Example 2.

Example 11: Preparation of Microcapsule Dispersions

Example 11 provides methods for preparation of microcapsule dispersions. An aqueous phase was prepared by mixing 0.45 g of a 10% by weight aqueous solution of Selvol™ 823 poly(vinyl alcohol) hydrolyzed to 87-89% (Sekisui), 21.6 g of 2-hydroxyethyl methacrylate Bisomer™ HEMA (Geo Chemicals) and 148.5 g of water.

An oil phase was prepared by mixing 1.35 g of lauroyl peroxide Luperox™ LP (Arkema), 26.5 g of ethylene glycol dimethacrylate SR 206 (Sartomer) and 135 g of fragrance (fragrance compositions C1, C2 and 1-6). This mixture was stirred until complete dissolution of lauroyl peroxide.

The aqueous phase and the oil phase were stirred together during 15 min with a stirrer bar and then, at 10,000 rpm for 1 min using a highshear mixer (Ystral X 10/20 E3-1050 W equipped with a Dispermix head of diameter 40/54 mm) to obtain an emulsion.

66.3 g of a 10% by weight aqueous solution of Selvol™ 823 poly(vinyl alcohol) hydrolyzed to 87-89% (Sekisui) were poured into a 500 mL-batch reactor equipped with a condenser, a thermometer or temperature probe, a nitrogen inlet and an anchor blade stirrer (diameter 4 cm). 323 g of the emulsion were added under stirring at 250 rpm. 0.32 g of tetraethylene pentaamine mixture (CAS N° 112-57-2) dissolved in 18.7 g of water were then added. Nitrogen was bubbled through the mixture. The emulsion was then heated to 70° C. over one hour. After 2 hours at 70° C., a solution containing 0.19 g of 2,2'-Azobis(2-methylpropionamidine) dihydrochloride in 5 g of water was added. After one additional hour, 1.03 g of Solagum™ AX (combination of Acacia Senegal gum & xanthan gum, Seppic) were added within 5 min. Finally, the resulting microcapsule dispersion was cooled to room temperature during 1 hour.

The median volume diameter (D(v; 0.5)), the span number and the solid content of the resultant microcapsule dispersions were determined according to the methods disclosed above. The median volume diameter of the microcapsules was in the range from about 26 to about 37 micrometers, with a span of about 0.6 The solid contents was in the range from about 43% to about 46%.

Example 12: Olfactive Test

The olfactive performance of microcapsules of the present disclosure was assessed on fabric washed with a liquid detergent containing an amount of capsule dispersion equivalent to 0.5 wt % of fragrance.

Specifically, cotton terry towels (20 pieces, 30 cm*20 cm, about 50 g) were washed with 60 g of detergent (standard liquid detergent) in a washing machine (Miele PW 6065 Vario) at 40° C. using the short cycle program. The wash was followed by a rinse at 1300 rpm without softener.

A panel of 16 trained assessors scored the olfactive intensity of the samples wet with minimal gentle handling, then after indoor line drying for 24 hour the intensity was assessed before and after rubbing. The results are summarised in Tables 3 and 4 below.

For each assessment, the panelists were asked to rate the intensity of the perfume perception on a scale ranging from 1 to 100, wherein 1 means no odour and 100 means very strong odour. The intensity was statistically treated by analysis of variance ANOVA (Confidence interval (%): 95, Tolerance: 0.0001).

TABLE 3

| Example | Fragrance composition | Wet Intensity | Dry Pre-Rub Intensity | Dry Post-Rub intensity |
|---|---|---|---|---|
| 3 | C1 | 25 | 7 | 46 |
| 4 | 1 | 33 | 8 | 51 |
| 5 | 2 | 40 | 6 | 59** |
| 6 | 3 | 36 | 5 | 52 |

TABLE 4

| Example | Fragrance composition | Wet Intensity | Dry Pre-Rub Intensity | Dry Post-Rub intensity |
|---|---|---|---|---|
| 7 | C2 | 30 | 6 | 39 |
| 8 | 4 | 27 | 7 | 42 |
| 9 | 5 | 29 | 4 | 53** |
| 10 | 6 | 28 | 6 | 45 |

It can be seen from Tables 3 and 4 that adding an accord including isopulegol, L-menthol and citroxide (sourced from lime oxide), rather than isopropyl myristate alone, to each of fragrance compositions A and B, resulted in an increase in perceived intensity at the dry stage after rubbing. This increase was significant (**) at the 95% confidence interval for the microcapsules containing 5 wt % of the said accord.

There was also an increase of the perceived intensity at the wet stage when the accord was added to fragrance composition A.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the device, method, and system of the disclosed subject matter without departing from the spirit or scope of the disclosed subject matter. Thus, it is intended that the disclosed subject matter include modifications and variations that are within the scope of the appended claims and their equivalents.

For any patents, patent applications, publications, product descriptions, and protocols are cited throughout this application, the disclosures of all of which are incorporated herein by reference in their entireties for all purposes.

The invention claimed is:

1. A laundry product comprising a fragrance composition encapsulated in core-shell capsules, wherein the fragrance composition comprises from about 1.00 wt % to about 10.00 wt %, based on the weight of the fragrance composition, of an accord, wherein the accord comprises:
   (i) from about 90.00 wt % to about 99.99 wt %, based on the weight of the accord, of at least one compound selected from the group consisting of menthol, menthyl acetate, isopulegol, pulegone, pulegol, peppermint cyclohexanone, dihydromyrcene and combinations thereof;
   (ii) from about 0.01 wt % to about 10.00 wt %, based on the weight of the accord, of at least one compound selected from the group consisting of citroxide, elemicin, elemol, geranic oxide, vanillyl ethyl ether, vanillyl butyl ether, caryophyllene beta, zingiberene alpha and combinations thereof;
   wherein the accord comprises at least two compounds,
   wherein at least one of menthol and isopulegol is present in the accord; and
   wherein the sum of (i)+(ii) makes up 100 wt % of the accord.

2. A laundry product comprising a fragrance composition encapsulated in core-shell capsules, wherein the fragrance composition comprises from about 1.00 wt % to about 10.00 wt %, based on the weight of the fragrance composition, of an accord, wherein the accord consists of menthol, isopulegol and citroxide;
   wherein menthol and isopulegol make up from about 90.00 wt % to about 99.99 wt % of the accord and citroxide makes up from about 0.01 wt % to about 10.00 wt % of the accord.

3. The laundry product of claim 1, wherein the accord comprises menthol and menthol represents at least 40.00 wt % of the combined weight of all compounds (i) in the accord.

4. The laundry product of claim 1, wherein the accord comprises isopulegol and isopulegol represents at least 40.00 wt % of the combined weight of all compounds (i) in the accord.

5. The laundry product of claim 1, wherein the accord comprises menthol and isopulegol and optionally at least one other compound (i), wherein the weight ratio between menthol and isopulegol is in the range from about 30:70 to about 70:30.

6. The laundry product of claim 5, wherein the sole compounds (i) of the accord are menthol and isopulegol.

7. The laundry product of claim 1, wherein the at least one compound (ii) is selected from the group consisting of elemicin, elemol and citroxide.

8. The laundry product of claim 1, wherein the shell of the core shell capsules comprises a material selected from the group consisting of: polyolefins, polyamides, polystyrenes, polyisoprenes, polycarbonates, polyesters, polyacrylates, aminoplasts, polysaccharides, gelatine, shellac, epoxy resins, vinyl polymers, water insoluble inorganics, silicone, and mixtures thereof.

9. The laundry product of claim 8 wherein the shell comprises melamine formaldehyde and/or cross-linked melamine formaldehyde.

10. The laundry product of claim 8, wherein the shell comprises a polyacrylate.

11. The laundry product of claim 8, wherein the shell is coated with a deposition aid.

12. The laundry product of claim 1, wherein the laundry product is selected from the group consisting of a laundry detergent, a fabric softener and a fabric conditioner.

13. The laundry product of claim 2, wherein the weight ratio between menthol and isopulegol is in the range from about 30:70 to about 70:30.

14. The laundry product of claim 2, wherein the shell of the core shell capsules comprises a material selected from the group consisting of: polyolefins, polyamides, polystyrenes, polyisoprenes, polycarbonates, polyesters, polyacrylates, aminoplasts, polysaccharides, gelatine, shellac, epoxy resins, vinyl polymers, water insoluble inorganics, silicone, and mixtures thereof.

15. The laundry product of claim 14, wherein the shell comprises melamine formaldehyde and/or cross-linked melamine formaldehyde.

16. The laundry product of claim 14, wherein the shell comprises a polyacrylate.

17. The laundry product of claim 14, wherein the shell is coated with a deposition aid.

18. The laundry product of claim 2, wherein the laundry product is selected from the group consisting of a laundry detergent, a fabric softener and a fabric conditioner.

\* \* \* \* \*